(12) United States Patent
Lally

(10) Patent No.: US 8,439,041 B2
(45) Date of Patent: May 14, 2013

(54) TRACHEAL TUBE WITH SCAFFOLDING-SUPPORTED WALL

(75) Inventor: Olaf Lally, Galway (IE)

(73) Assignee: Covidien LP, Mansfield, MA (US)

( * ) Notice: Subject to any disclaimer, the term of this patent is extended or adjusted under 35 U.S.C. 154(b) by 402 days.

(21) Appl. No.: 12/750,789

(22) Filed: Mar. 31, 2010

(65) Prior Publication Data
US 2011/0240033 A1 Oct. 6, 2011

(51) Int. Cl.
*A61M 16/04* (2006.01)
(52) U.S. Cl.
USPC .................................................. 128/207.14
(58) Field of Classification Search ............. 128/200.26, 128/207.14, 207.15, 911
See application file for complete search history.

(56) References Cited

U.S. PATENT DOCUMENTS

| | | | |
|---|---|---|---|
| 3,945,385 A | 3/1976 | Sackner | |
| 3,964,488 A | 6/1976 | Ring et al. | |
| 4,141,364 A * | 2/1979 | Schultze | 128/207.15 |
| 4,305,392 A | 12/1981 | Chester | |
| 5,245,992 A | 9/1993 | Nye | |
| 5,333,608 A | 8/1994 | Cummins | |
| 5,611,336 A | 3/1997 | Page et al. | |
| 5,730,123 A | 3/1998 | Lorenzen et al. | |
| 5,772,639 A | 6/1998 | Lampropoulos et al. | |
| 5,819,723 A | 10/1998 | Joseph | |
| 6,796,309 B2 | 9/2004 | Nash et al. | |
| 6,849,042 B2 | 2/2005 | Christopher | |
| 6,860,264 B2 | 3/2005 | Christopher | |
| 7,478,636 B2 | 1/2009 | Madsen et al. | |
| 7,503,328 B2 | 3/2009 | Kolobow et al. | |
| 7,581,541 B2 | 9/2009 | Madsen et al. | |
| 7,682,538 B2 * | 3/2010 | Ohigawa et al. | 264/177.1 |
| 8,182,500 B2 * | 5/2012 | Hoary et al. | 606/159 |
| 2004/0221853 A1 | 11/2004 | Miller | |
| 2005/0033225 A1 | 2/2005 | Wu et al. | |
| 2005/0229933 A1 | 10/2005 | McGrail et al. | |
| 2007/0028924 A1 | 2/2007 | Madsen et al. | |
| 2007/0028925 A1 | 2/2007 | Madsen et al. | |
| 2008/0078405 A1 * | 4/2008 | Crumback et al. | 128/207.15 |

FOREIGN PATENT DOCUMENTS

| | | |
|---|---|---|
| WO | 03/101516 A1 | 12/2003 |
| WO | 2006113544 A2 | 7/2011 |

OTHER PUBLICATIONS

T. Kolobow, et al.; "The Mucus Slurper: a novel tracheal tube that requires no tracheal tube suctioning. A Preliminary Report."; Intensive Care Medicine, vol. 32, pp. 1414-1418 (2006).
G.L. Bassi et al.; "A 72-hour study to test the efficacy and safety of the "Mucus Slurper" in mechanically ventilated sheep"; Crit Care Med, vol. 35, No. 3, pp. 906-911 (2007).
R.D. Branson, "Secretion Management in the Mechanically Ventilated Patient"; Respiratory Care, vol. 52, No. 10, Oct. 2007, pp. 1328-1347.
International Search Report and Written Opinion for PCT Application No. PCT/US2011/028113 dated Jun. 22, 2011, 14 pgs.

* cited by examiner

*Primary Examiner* — Jackie Ho
*Assistant Examiner* — Mark Wardas

(57) ABSTRACT

Various embodiments of a medical device tube having scaffolding-supported inner and outer walls are provided. In particular, the medical device tube may include a plurality of struts extending from an inner wall to an outer wall of the medical device tube. In certain embodiments, each of the individual struts may connect to adjacent struts at the inner wall and the outer wall. As such, the plurality of struts may comprise a zigzag pattern circumferentially around the medical tube device. In other embodiments, the struts may extend radially from the inner wall to the outer wall of the medical tube device. Regardless, the area between the struts and the inner wall and/or the outer wall form a plurality of lumens, which may be used for suctioning, blowing, and various other applications of the medical device tube.

14 Claims, 8 Drawing Sheets

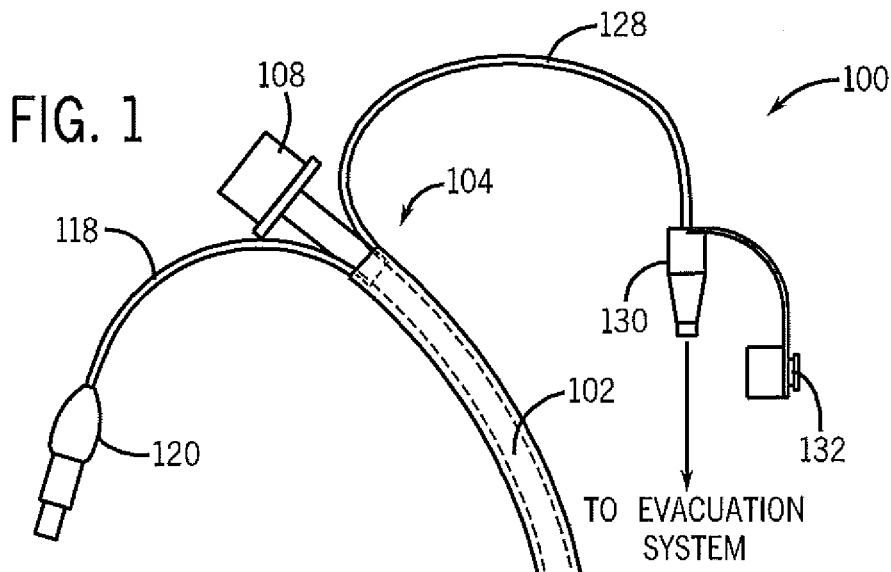
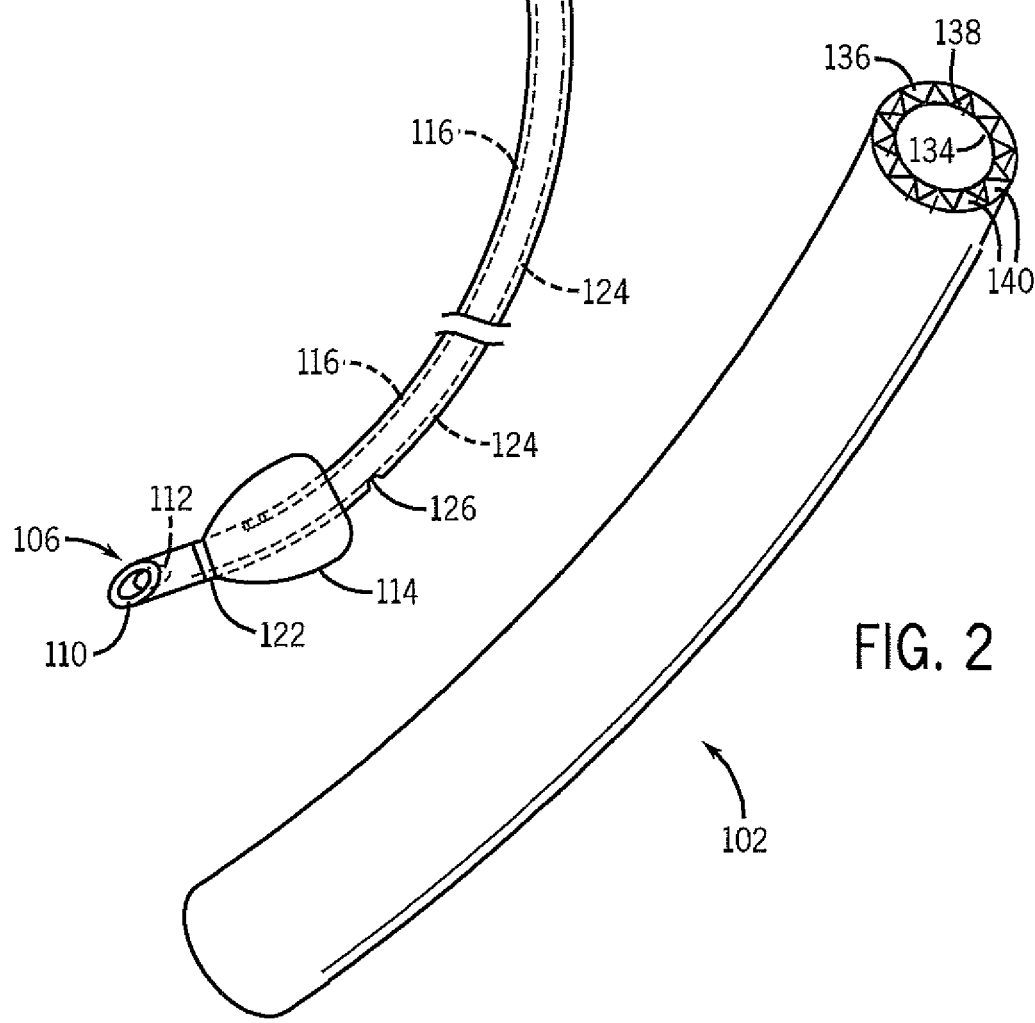

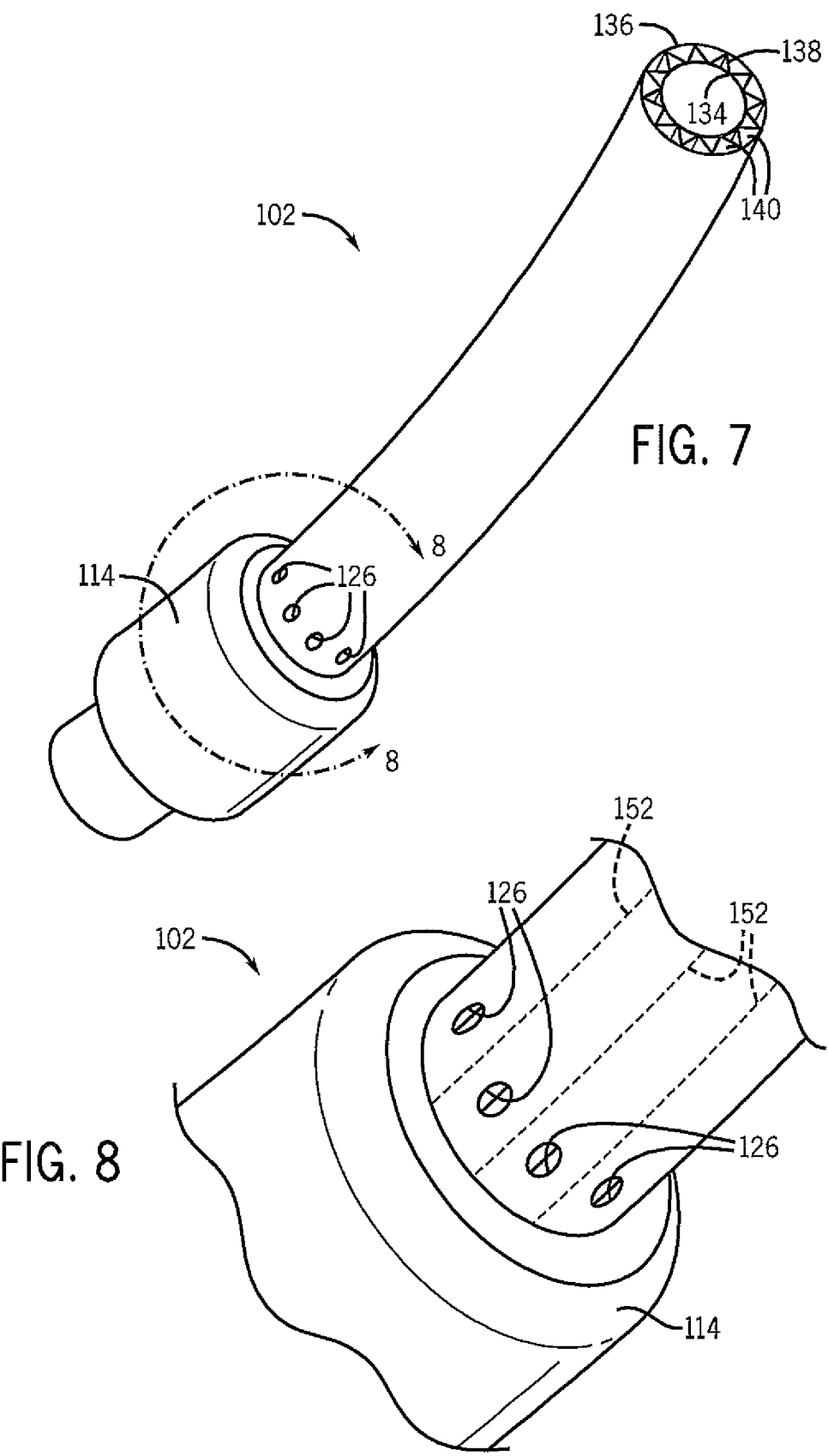

TRACHEAL TUBE WITH SCAFFOLDING-SUPPORTED WALL

BACKGROUND

The present disclosure, according to certain embodiments, relates to tubular devices used in medical applications, and more particularly, to tracheal tubes having scaffolding-supported inner and/or outer walls.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, various tubular devices may be used to control the flow of air, food, fluids, or other substances into and out of the patient. For example, medical devices, such as tracheal tubes, may be used to control the flow of air or other gases through a trachea of a patient, such as via artificial ventilation. Such tracheal tubes may include endotracheal tubes (ETTs), tracheostomy tubes, or transtracheal tubes. Tubular devices of this type typically have a fairly large central opening extending along their length through which air (or other gases) may be channeled. Many of the tubes also have one or more much smaller channels, typically referred to as lumens, formed in their walls. Where provided, such lumens are often devoted to a particular purpose, and the tubes themselves are specifically designed to function with the dedicated lumens. If needs differ, the number, size, and location of such lumens also differ insomuch as the tubes are specifically designed to include only those lumens required.

For example, in many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient. In addition, a high-quality seal against the tracheal passageway allows a ventilator to perform efficiently. An inflatable cuff typically serves this purpose, and a dedicated lumen is typically provided that terminates inside the cuff to allow for inflation air to be introduced into the cuff after intubation.

As another example, in many instances, it is also desirable to manage the accumulation of subglottic secretions (e.g., mucus) around the seal (e.g., a cuff) via removal through external suctioning, administration of antibiotics, or a combination thereof. These subglottic secretions are undesirable as they contain bacteria that may cause infection if left to grow. In addition, the subglottic secretions may cause ventilator-associated pneumonia (VAP) due to bacterial colonization of the lower respiratory airways. As such, the tracheal tubes may include one or more dedicated lumens extending axially through walls of the tracheal tubes, which are ported at desired locations where the secretions may collect, allowing simple removal via suction through the lumen.

In still other applications, dedicated lumens may allow for suctioning and blowing for other purposes (e.g., medicament administration), or for the deployment of various devices, such as cameras, devices for monitoring pressure, temperature, and other parameters. Again, where such lumens are needed, a special tube is developed, and if not needed, the basic tube design eliminates them.

BRIEF DESCRIPTION OF THE DRAWINGS

Advantages of the disclosed techniques may become apparent upon reading the following detailed description and upon reference to the drawings in which:

FIG. 1 is a perspective view of an exemplary endotracheal tube, which may use a multifunction medical tube having scaffolding-supported inner and outer walls;

FIG. 2 is a perspective view of an exemplary multifunction medical device tube having scaffolding-supported inner and outer walls of a type that may be used in the tube of FIG. 1;

FIG. 7 is a perspective view of the medical tube device having ports in the outer wall of the medical device tube that correspond to lumens abutting the outer wall;

FIG. 8 is another perspective view of an exemplary multifunction medical tube device having ports in the outer wall in connection with lumens formed in the tube body;

DETAILED DESCRIPTION OF SPECIFIC EMBODIMENTS

Figure 3:
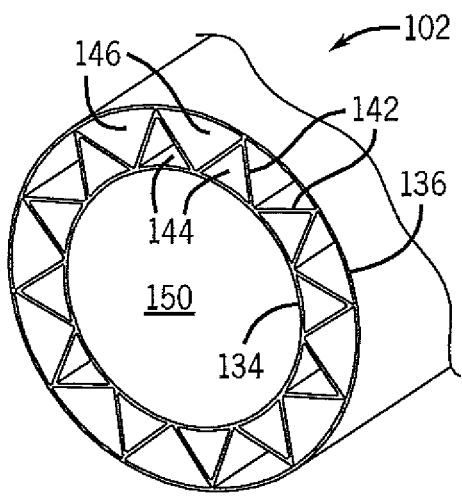
FIG. 3 is a cross-sectional view of the multifunction medical device tube of FIG. 2.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As discussed in detail below, various embodiments are provided of a medical device tube having scaffolding-supported inner and outer walls. In particular, the medical device tube may include a plurality of struts extending from an inner wall to an outer wall of the medical device tube. In certain embodiments, each of the individual struts may connect to adjacent struts at the inner wall and the outer wall. As such, the plurality of struts may comprise a zigzag pattern circumferentially around the medical tube device. In other embodiments, the struts may extend radially from the inner wall to the outer wall of the medical tube device. Regardless, the area between the struts and the inner wall and/or the outer wall form a plurality of lumens, which may be used for suctioning, blowing, and various other applications of the medical device tube. As such, the medical device tube is a pre-formed, fully radial, multifunction tube.

The resulting structure may be termed a "multifunction" tube that may serve a range of applications for which dedicated lumens were used in the past. Although several models may be made and used, it is particularly attractive to consider the tube itself as a "generic" tube in which lumens or passageways are formed radially around a central opening. These may be used in particular applications, left unused, plugged, ported, or otherwise adapted for such applications from the basic generic structure.

The devices and techniques provided herein may enable the manufacturing of a medical device tube having a standard cross-sectional profile and providing a plurality of lumens that may be used for suctioning, blowing, introducing cameras, introducing sensors, and so forth, into the airway of a patient. In particular, the plurality of lumens will be formed between the struts and the inner wall and/or outer wall of the multifunction medical device tube. As such, dedicated lumens need not be manufactured into walls for specific applications. Rather, the plurality of lumens may be available when needed. Conversely, when not needed, individual lumens may be plugged or otherwise bypassed. In addition, having the plurality of lumens extend 360 degrees circumferentially (i.e., fully radially) around the medical device tube ensures various applications may be well served (e.g., for evacuation applications, such that secretions may be removed no matter what orientation the patient is lying). Forming the plurality of lumens using the area between the inner and outer walls of the medical device tube may also maximize the cross-sectional area used for certain applications (e.g., suctioning and evacuation). Furthermore, the struts will function as a support structure, preventing collapse of the inner and outer wall of the medical device tube.

Turning now to the drawings, FIG. 1 is a perspective view of an exemplary endotracheal tube 100, which may use a multifunction medical device tube 102 having scaffolding-supported inner and outer walls. Although illustrated as being used in the endotracheal tube 100, the multifunction medical device tube 102 may be used in tracheostomy tubes, transtracheal tubes, or any other suitable tracheal tubes. The endotracheal tube 100 has proximal and distal ends 104 and 106. In the illustrated embodiment, the proximal end 104 may be outfitted with a connector 108 that may be attached to a mechanical ventilator during operation. The distal end 106 terminates in an opening 110 and may be placed in a patient's trachea during operation to maintain airflow to and from the patient's lungs. A Murphy's eye 112 may be located on the endotracheal tube 100 opposite the opening 110 to prevent airway occlusion when the endotracheal tube 100 is improperly placed within the patient's trachea.

As illustrated, an inflation cuff 114 that may be inflated to seal against the walls of a body cavity (e.g., a trachea) may be attached to the distal end 106 of the endotracheal tube 100. The inflation cuff 114 may be inflated via an inflation lumen 116 terminating in an inflation tube 118 connected to a fixture 120. A shoulder 122 of the inflation cuff 114 may secure the inflation cuff 114 to the endotracheal tube 100. In certain embodiments, the shoulder 122 may be folded up inside a lower end of the inflation cuff 114. As illustrated, the endotracheal tube 100 also includes a suction lumen 124 that extends from a location on the endotracheal tube 100 positioned outside the body when in use to a location on the endotracheal tube 100 above the inflation cuff 114. The suction lumen 124 terminates in a port 126 through which secretions may be aspirated. An exterior suction tube 128 connects to the suction lumen 124 for the removal of suctioned fluids. The suction tube 128 terminates outside the body during use in a fixture 130 with a cap 132 that allows the suction tube 128 to be connected to auxiliary equipment (e.g., vacuum, collection reservoir, and so forth) during evacuation, suctioning, blowing, or other applications.

As described in greater detail below, the inflation lumen 116 and the suction lumen 124 may be formed between an inner wall, outer wall, and support structures between the inner and outer wall of the medical device tube 102. Indeed, the lumens formed between the inner wall, outer wall, and the support structures may be used for various applications related to the medical device tube 102. In addition, as described in greater detail below, the connector 108 may be configured to connect the inflation lumen 116 and the suction lumen 124 to the inflation tube 118 and the exterior suction tube 128, respectively. Although illustrated as extending through the proximal end 104 of the medical device tube 102, in certain embodiments, the inflation lumen 116 and the suction lumen 124 may be accessed at any point along the medical device tube 102.

FIG. 2 is a perspective view of an exemplary multifunction medical device tube 102 having scaffolding-supported inner and outer walls, of a type that may be used in the product shown in FIG. 1, as well as in a range of other applications. In particular, as illustrated in FIG. 2, the medical device tube 102 includes an inner wall 134, an outer wall 136, and a scaffolding frame 138. The medical device tube 102 may have a substantially constant cross-sectional profile, for instance, with a substantially constant inner wall 134 cross-sectional profile, substantially constant outer wall 136 cross-sectional profile, and a substantially constant scaffolding frame 138 cross-sectional profile. As illustrated, the medical device tube 102 may be manufactured via appropriate manufacturing techniques (e.g., extrusion) and may be cut to appropriate lengths, depending on the particular application for which the medical device tube 102 is used.

As described in greater detail below, the scaffolding frame 138 of the medical device tube 102 may define a plurality of lumens within the inner wall 134 and the outer wall 136 of the medical device tube 102. More specifically, as opposed to conventional medical device tubes, which are generally comprised of solid materials between their inner walls and outer walls, the medical device tube 102 described herein may have a plurality of lumens 140 defined between the scaffolding frame 138 and the inner wall 134 and/or the outer wall 136 of the medical device tube 102. In other words, the area between the scaffolding frame 138 and the inner wall 134 and/or the outer wall 136 of the medical device tube 102 may not be filled with tubing material. Rather, the area between the scaffolding frame 138 and the inner wall 134 and/or the outer wall 136 of the medical device tube 102 may be reserved as passageways (e.g., the lumens 140) through the inner wall 134 and outer wall 136 that extend axially along the medical device tube 102. As such, the medical device tube 102 may be manufactured as a pre-formed, fully radial, multifunction tube.

As described above, the scaffolding frame 138 may have a substantially constant cross-sectional profile. FIG. 3 is a cross-sectional view of the medical device tube 102 of FIG. 2. As illustrated, in certain embodiments, the scaffolding frame 138 may include a series of struts 142, wherein each individual strut 142 is connected to adjacent struts 142 at either the inner wall 134 or the outer wall 136. As such, the struts 142 generally form a zigzag pattern around the entire circumference of the medical device tube 102.

In the illustrated embodiment, the plurality of lumens 140 may include a plurality of inner lumens 144 between the inner wall 134 and the struts 142 and a plurality of outer lumens 146 between the outer wall 136 and the struts 142. Both the plurality of inner lumens 144 and the plurality of outer lumens 146 are fully radial. In other words, both the plurality of inner lumens 144 and the plurality of outer lumens 146 extend 360 degrees circumferentially around the medical device tube 102. In the illustrated embodiment, the zigzag nature of the struts 142 (e.g., with each individual strut 142 connected to adjacent struts 142 at either the inner wall 134 or the outer wall 136) creates inner and outer lumens 144, 146 that are generally triangular in shape. However, as described below, other arrangements of struts 142 may create inner and outer lumens 144, 146 having other shapes.

Figure 4:
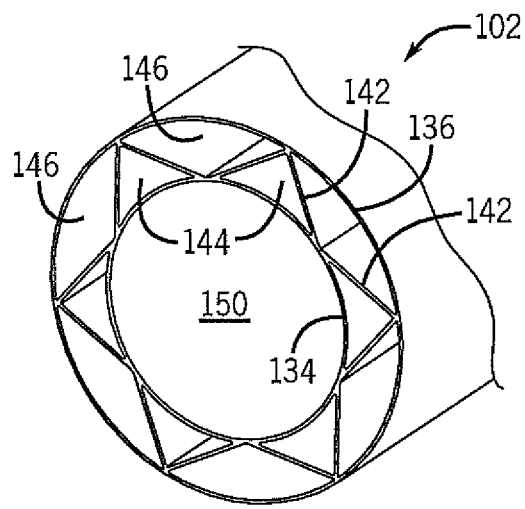
FIG. 4 is a cross-sectional view of an alternative multifunction medical device tube having fewer lumens than that illustrated in FIG. 3.

In addition, the illustrated embodiment includes twelve generally triangular-shaped inner lumens 144 and twelve generally triangular-shaped outer lumens 146. However, other embodiments may include more or fewer inner and outer lumens 144, 146. For example, FIG. 4 is a cross-sectional view of an alternative medical device tube 102 having fewer lumens 140 than that illustrated in FIG. 3. More specifically, as illustrated in FIG. 4, the medical device tube 102 includes six generally triangular-shaped inner lumens 144 and six generally triangular-shaped outer lumens 146, as opposed to the embodiment illustrated in FIG. 3, which includes twelve generally triangular-shaped inner lumens 144 and twelve generally triangular-shaped outer lumens 146. However, in certain embodiments, the struts 142 disposed in a zigzag pattern circumferentially around the medical device tube 102 may form four, five, six, seven, eight, nine, ten, eleven, twelve, or even more generally triangular-shaped inner and outer lumens 144, 146 between the inner wall 134 and the outer wall 136.

Figure 5:
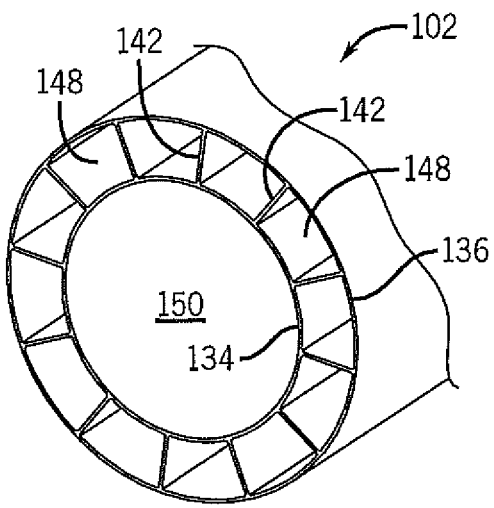
FIG. 5 is a cross-sectional view of another alternative multifunction medical device tube having struts that extend radially from an inner wall to an outer wall.

In addition, the embodiments of the medical device tube 102 illustrated in FIG. 3 and FIG. 4 both include struts 142 that zigzag between the inner wall 134 and the outer wall 136 (e.g., with each individual strut 142 connected to adjacent struts 142 at either the inner wall 134 or the outer wall 136). However, other embodiments of the medical device tube 102 may include struts 142 that are not disposed in a zigzag pattern between the inner wall 134 and the outer wall 136. For example, FIG. 5 is a cross-sectional view of another alternative medical device tube 102 having struts 142 that extend radially from the inner wall 134 to the outer wall 136 of the medical device tube 102. As such, the plurality of lumens 140 will not include a plurality of inner lumens 144 and a plurality of outer lumens 146. Rather, the plurality of lumens 140 will include a plurality of generally rectangular-shaped or, depending on the number of struts 142, trapezoidal-shaped lumens 148. In the illustrated embodiment, each individual lumen 148 is formed between the inner wall 134, the outer wall 136, and two adjacent struts 142. Again, the plurality of lumens 148 formed between the inner wall 134, the outer wall 136, and the adjacent struts 142 are fully radial. In other words, the plurality of lumens 148 extend 360 degrees circumferentially around the medical device tube 102. Again, the number of generally rectangular-shaped or trapezoidal-shaped lumens 148 formed by the struts 142 extending radially between the inner wall 134 and the outer wall 136 of the medical device tube 102 may vary between embodiments and may be four, five, six, seven, eight, nine, ten, eleven, twelve, or even more.

Figure 6:
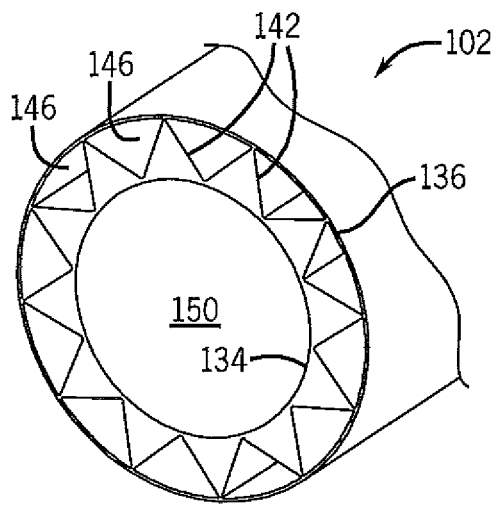
FIG. 6 is a cross-sectional view of a further alternative multifunction medical device tube having a plurality of outer lumens but no inner lumens.

In addition, the embodiments illustrated in FIG. 3 and FIG. 4 include both a plurality of inner lumens 144 and a plurality of outer lumens 146, wherein both the inner lumens 144 and the outer lumens 146 are defined by the area between adjacent struts 142 and the inner wall 134 or the outer wall 136, respectively. However, in other embodiments, the plurality of inner lumens 144 may not be formed between the inner wall 134 and the struts 142. For example, FIG. 6 is a cross-sectional view of a further alternative medical device tube 102 having a plurality of outer lumens 146 but no inner lumens 144. Rather, in the embodiment illustrated in FIG. 6, the area between the struts 142 and the inner wall 134 may be filled with tubing material. More specifically, in this embodiment, the area that would otherwise form the inner lumens 144 may not be extruded from the medical device tube 102. One reason for filling in the area that would otherwise represent the inner lumens 144 is that suctioning, blowing, and/or other applications are generally not required within the inner wall 134 of the medical device tube 102 because the interior volume 150 within the inner wall 134 of the medical device tube 102 is typically open from a distal end of the medical device tube 102 to a proximal end of the medical device tube 102. However, in certain embodiments, one or only a few of the inner lumens 144 may be extruded, with these few inner lumens 144 being used for such applications as an inflation lumen 116 for inflating an inflation cuff 114 at a distal location of the medical device tube 102, or as a radiopaque line by, for example, being filled with barium sulfate or another similar substance.

As opposed to the inner lumens 144, because the outer lumens 146 of FIG. 6 (as well as the outer lumens 146 of FIGS. 3 and 4 and the lumens 148 of FIG. 5) are at least partially formed by the outer wall 136 of the medical device tube 102, these lumens 140 may be more useful for evacuation, suctioning, blowing, and/or other applications. In other words, these lumens 140 may be adjacent to areas outside of the outer wall 136 of the medical device tube 102 where evacuation, suctioning, blowing, and/or other applications may prove beneficial. For example, the areas outside of the outer wall 136 of the medical device tube 102 may be adjacent to a proximal side of an inflation cuff 114 of the medical device tube 102, wherein the inflation cuff 114 forms a seal against the patient's trachea. As such, subglottic secretions may form outside of the outer wall 136 of the medical device tube 102. Therefore, the ability to suction or blow through the lumens 140 abutting the outer wall 136 of the medical device tube 102 may prove beneficial.

In order to expose the lumens 140 abutting the outer wall 136 to areas outside of the outer wall 136, the medical device tube 102 may include notches or ports in the outer wall 136 which generally correspond to the lumens 140. Similarly, the lumens 140 abutting the inner wall 134 may also include ports in the inner wall 134. FIG. 7 is a perspective view of the medical tube device 102 having ports 126 in the outer wall 136 of the medical device tube 102 that correspond to lumens 140 abutting the outer wall 136. FIG. 7 specifically illustrates a medical device tube 102 having a cross-sectional profile similar to that illustrated in FIG. 3. However, in other embodiments, the medical device tube 102 may include other cross-sectional profiles as described herein.

As illustrated, the ports 126 may be circular holes. However, the ports 126 may include other shapes. In certain embodiments, the ports 126 may be located on the medical device tube 102 on a proximal side of an inflation cuff 114. The inflation cuff 114 may be inflated to provide a seal between the medical device tube 102 and the patient. Because the ports 126 are located on a proximal side of the inflation cuff 114, subglottic secretions that accumulate around the inflation cuff 114 may be suctioned through the ports 126 and the lumens 140 abutting the outer wall 136 of the medical device tube 102. In addition, air and other fluids (e.g., antibiotics) may be introduced through the lumens 140 and the ports 126 to minimize the growth of bacteria.

FIG. 8 is another perspective view of the medical tube device 102 having ports 126 in the outer wall 136 of the medical device tube 102 in connection with lumens 140 formed in the tube body. In particular, FIG. 8 illustrates in greater detail how the ports 126 generally align between lines 152 that are defined by points in the cross-sectional profile of the medical device tube 102 where the struts 142 are connected to the outer wall 136 of the medical device tube 102.

Figure 9:
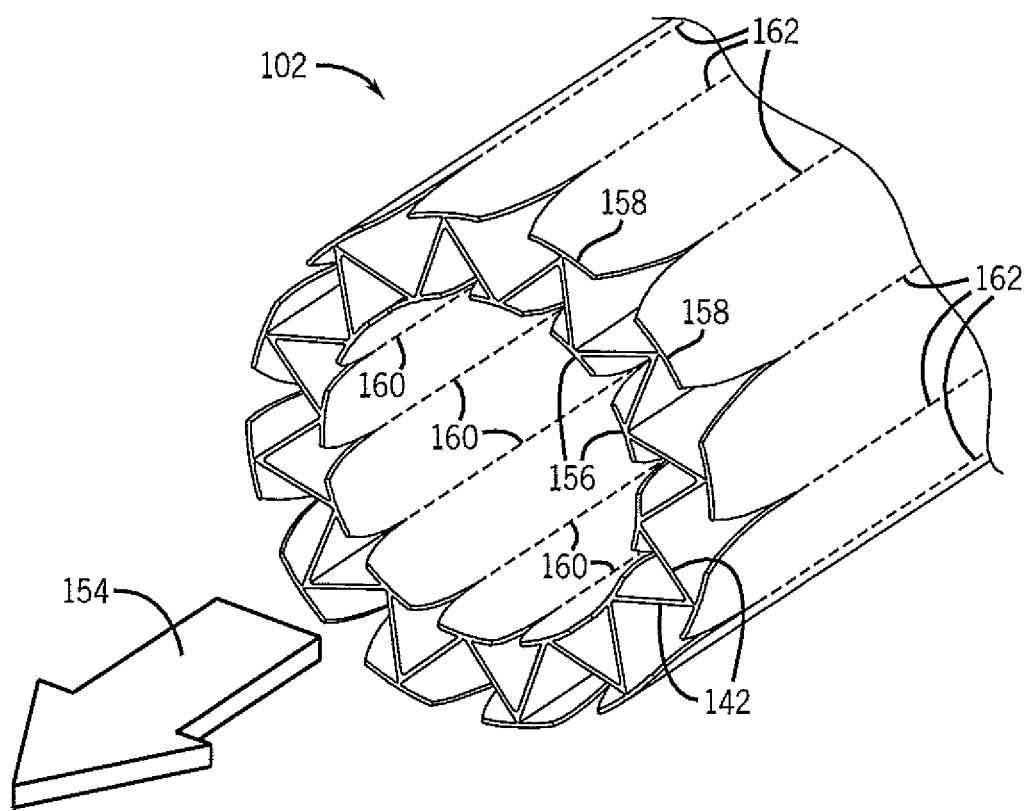
FIG. 9 is a perspective view of an exemplary multifunction medical device tube being progressively formed, such as by extruding.

As described above, the lumens 140 are defined by the area between the struts 142 and the inner wall 134 and/or the outer wall 136 of the medical device tube 102. As also described above, the medical device tube 102 may include a substantially constant cross-sectional profile. As such, one possible method of manufacturing the medical device tube 102 may be to use extrusion techniques. For example, FIG. 9 is a perspective view of the medical device tube 102 being progressively formed, such as by extruding. In particular, FIG. 9 illustrates the medical device tube 102 being extruded to have a cross-sectional profile similar to that illustrated in FIG. 3. In other words, the extruded medical device tube 102 of FIG. 9 may include a plurality of struts 142 with each individual strut 142 connected to adjacent struts 142 at either the inner wall 134 of the medical device tube 102 or the outer wall 136 of the medical device tube 102.

As illustrated, as the medical device tube 102 is extruded in the direction illustrated by arrow 154, the plurality of inner wall sections 156 between adjacent struts 142 and the plurality of outer wall sections 158 between adjacent struts 142 may be disconnected by small distances. However, as the extrusion continues in the direction of arrow 154, the plurality of inner wall sections 156 may be fused together forming inner progressive welds 160 due to the tendency of the tubing material to adhere to other nearby tubing material during the extrusion process. Similarly, the plurality of outer wall sections 158 may be fused together forming outer progressive welds 162. The other types of cross-sectional profiles described herein may be similarly extruded.

When using extrusion techniques as illustrated in FIG. 9, the inner wall 134, outer wall 136, and struts 142 of the medical device tube 102 may be made from the same material, which may be any material suitable for use in medical device tubes. For example, in certain embodiments, the medical device tube 102 may be made of polyurethane, polyvinyl chloride (PVC), polyethylene teraphthalate (PETP), low-density polyethylene (LDPE), polypropylene, silicone, neoprene, polytetrafluoroethylene (PTFE), or polyisoprene.

However, extrusion is not the only manufacturing technique that may be employed to create the medical device tube 102 described herein. For example, in certain embodiments, the struts 142 may be made of a different material than the inner and outer walls 134, 136 of the medical device tube 102. For instance, the inner and outer walls 134, 136 may be made of the materials described above. However, the struts 142 of the medical device tube 102 may be made from a different material than the inner and outer walls 134, 136 of the medical device tube 102. For example, the struts 142 of the medical device tube 102 may be made out of metals or metal alloys, such as stainless steel, tin, or aluminum. As such, the struts 142 may be visible in X-ray images of an anatomy through which the medical device tube 102 passes. In such an embodiment, more complex manufacturing techniques may be employed to connect the struts 142 to the inner and outer walls 134, 136 of the medical device tube 102.

The medical device tube 102 may also include additional longitudinal support structures for added strength. For example, in certain embodiments, the medical device tube 102 may include metal rods in the inner walls 134 and/or outer walls 136. Additionally, in certain embodiments, the medical device tube 102 may include metal rods that are threaded through lumens 140 that are not used for other applications.

As described above, the medical device tube 102 may be manufactured having a substantially constant cross-sectional profile of struts 142, inner wall 134, and outer wall 136. As such, the medical device tube 102 may include the plurality of lumens 140 extending axially along the medical device tube 102, and may be cut to appropriate lengths for use in various applications that would benefit from the plurality of lumens 140. In addition, the medical device tube 102 may be combined with other tube sections, connectors, and other devices. For example, in certain embodiments, the medical device tube 102 described herein may be connected to another tube, which may be more suitable for insertion into a patient's airway.

Figure 10:
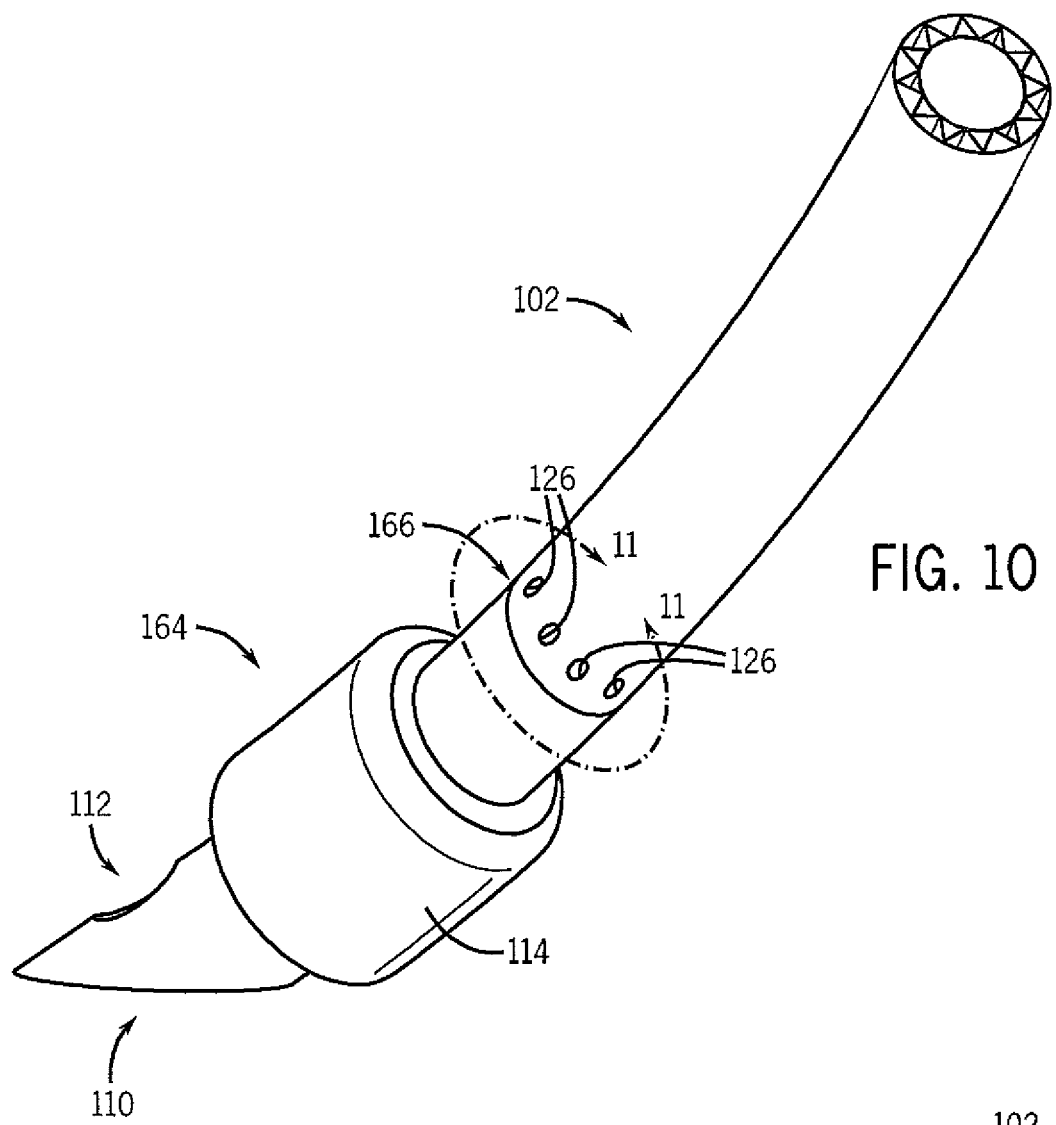
FIG. 10 is a perspective view of an exemplary multifunction medical device tube attached to a complementary distal tube section.

FIG. 10 is a perspective view of the medical device tube 102 attached to a complementary distal tube section 164. The distal tube section 164 may be more like conventional medical device tubes, for example, having solid walls. As illustrated, the distal tube section 164 terminates at a curved opening 110 and may be placed in a patient's trachea during operation to maintain airflow to and from the patient's lungs. A Murphy's eye 112 may be located on the distal tube section 164 opposite the opening 110 to prevent airway occlusion when the distal tube section 164 is improperly placed within the patient's trachea. In addition, the distal tube section 164 includes an inflation cuff 114, which may be used to form a seal between the distal tube section 164 and the patient's trachea. As illustrated, the medical device tube 102 and the distal tube section 164 may be attached at a distal end 166 of the medical device tube 102. The medical device tube 102 and the distal tube section 164 may be attached using any suitable attachment technique, such as bonding.

Figure 11:
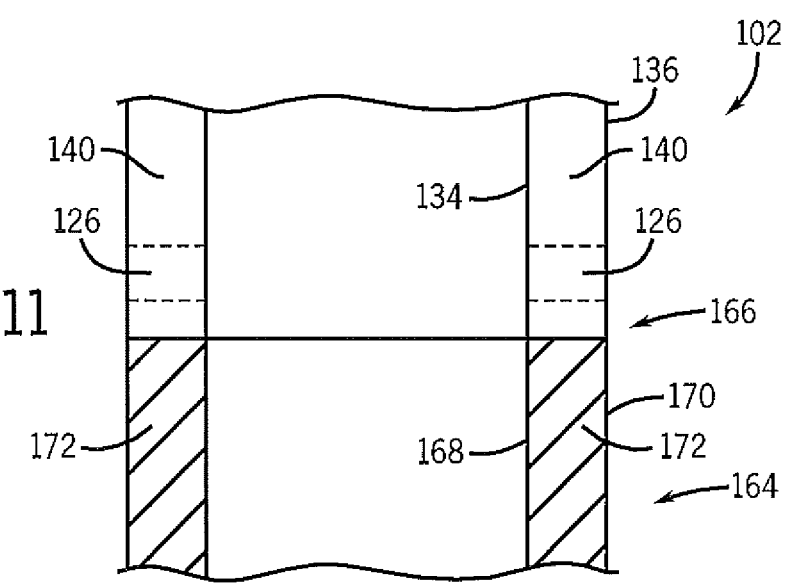
FIG. 11 is a cross-sectional side view of an exemplary multifunction medical device tube attached to the complementary distal tube section.

FIG. 11 is a cross-sectional side view of the medical device tube 102 attached to the distal tube section 164. As illustrated, the inner wall 134 of the medical device tube 102 is attached to an inner wall 168 of the distal tube section 164, and the outer wall 136 of the medical device tube 102 is attached to an outer wall 170 of the distal tube section 164. However, the area 172 between the inner wall 168 and the outer wall 170 of the distal tube section 164 is filled with tubing material. As such, the tubing material between the inner wall 168 and the outer wall 170 of the distal tube section 164 acts as a termination point for the plurality of lumens 140 at the distal end 166 of the medical device tube 102, where the medical device tube 102 and the distal tube section 164 are attached. Therefore, the plurality of lumens 140 may only be open to proximal portions of the medical device tube 102 through the plurality of ports 126 described above. However, in certain embodiments, the distal tube section 164 may include one or a few lumens that generally align with one or a few of the lumens 140 of the medical device tube 102. For example, an inflation lumen in the distal tube section 164, which is connected to the inflation cuff 114, may align with one of the lumens 140 of the medical device tube 102.

Figure 12:
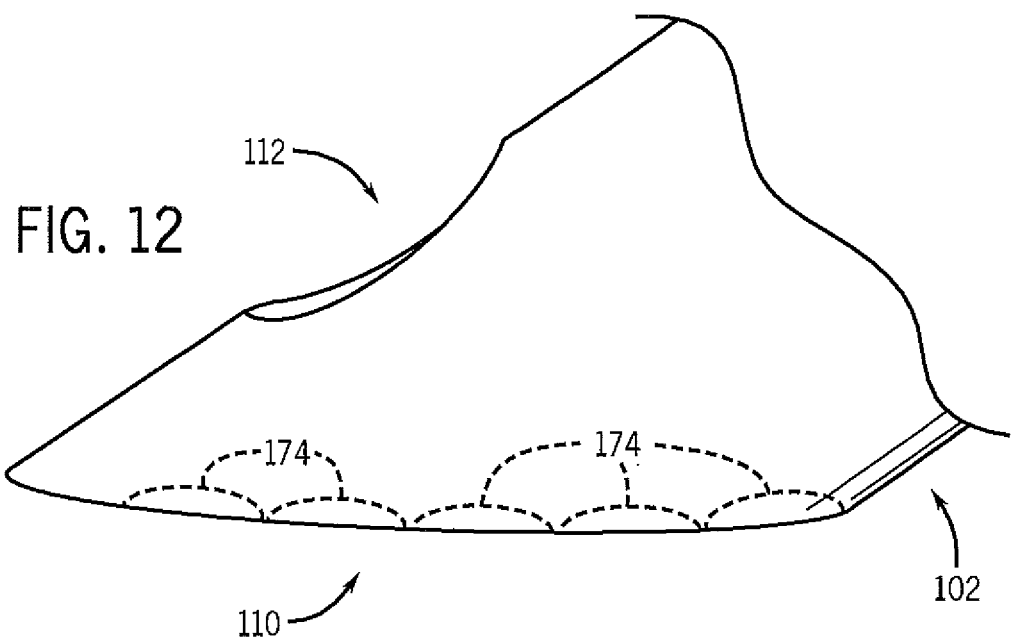
FIG. 12 is a side view of an exemplary multifunction medical device tube having various features of conventional tubes, such as a curved opening and a Murphy's eye near a distal end.

Another method of incorporating features such as the curved opening 110 and the Murphy's eye 112 into the medical device tube 102 may be to cut these features into the medical device tube 102. For example, FIG. 12 is a side view of the medical device tube 102 having various features, such as the curved opening 110 and the Murphy's eye 112 formed out of a distal end of the medical device tube 102. However, doing so would leave the plurality of lumens 140 extending to the distal end of the medical device tube 102. In other words, the plurality of lumens 140 would not terminate, precluding suctioning and blowing through the plurality of ports 126. In certain embodiments, this may be addressed by plugging the plurality of lumens 140 with a plurality of plugs 174 at a distal end of the medical device tube 102. In certain embodiments, the plurality of plugs 174 may be mechanical plugs that are, for example, interference fit into the plurality of lumens 140. However, in other embodiments, the plurality of plugs 174 may be created by melting and forming tubing material into the plurality of lumens 140. It should also be noted that, in certain embodiments, some of the lumens 140 may not be plugged but, rather, may be used to provide additional cross-sectional area in the medical device tube 102 for passing air into the airway of the patient.

Figure 13:
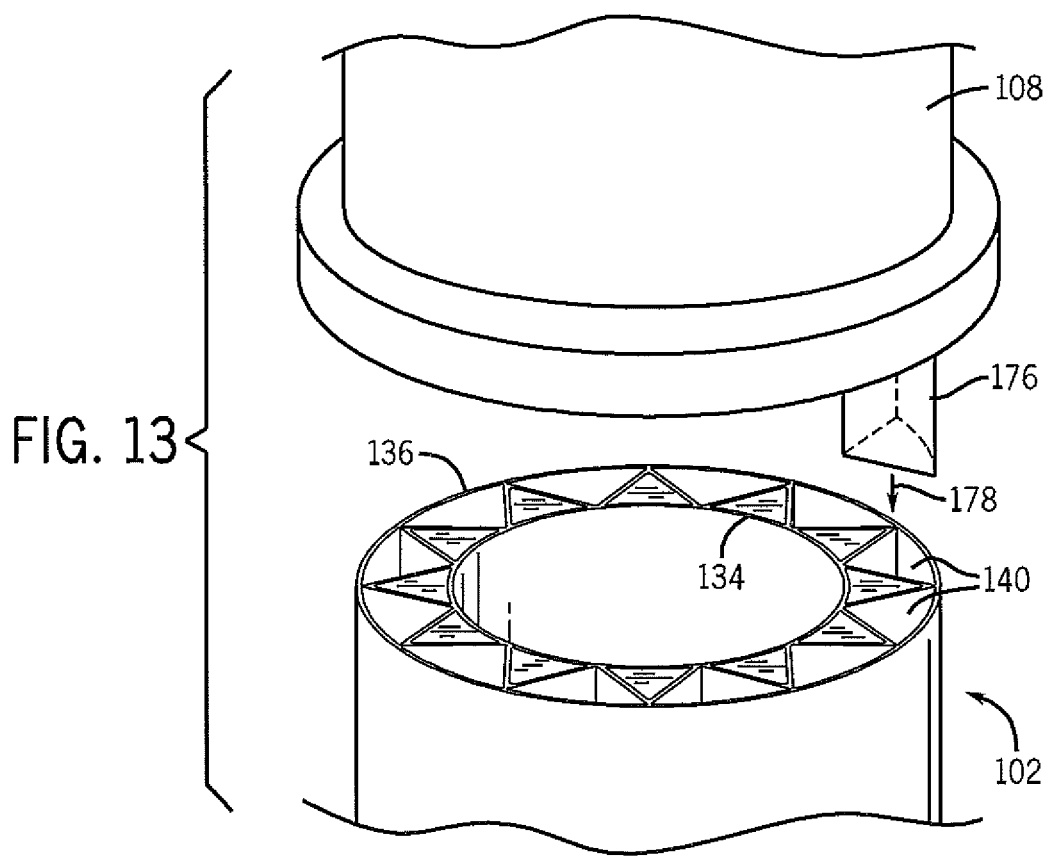
FIG. 13 is a perspective view of an exemplary connector configured to attach to the multifunction medical device tube.

As described above, the plurality of lumens 140 created between the inner wall 134 and the outer wall 136 of the medical device tube 102 may be used for suctioning, blowing, and other applications related to medical device tubes. As such, the proximal end of the medical device tube 102 will be configured to interact with other medical devices, such as connectors configured to attach the medical device tube 102 to apparatuses for suctioning, blowing, and other applications. For example, FIG. 13 is a perspective view of a connector 108 configured to attach to the medical device tube 102. The medical device tube 102 illustrated in FIG. 13 includes a cross-sectional profile similar to that of the embodiment illustrated in FIG. 6. However, any of the other cross-sectional profiles described herein may be used.

As illustrated, the connector 108 may include prongs 176 configured to be inserted into the plurality of lumens 140, as illustrated by arrow 178. Although illustrated as only including one prong 176, the connector 108 may have up to the number of lumens 140. In certain embodiments, the prongs 176 may be configured to be interference fit within the lumens 140. However, in other embodiments, the prongs 176 may be secured within the lumens 140 using other attachment techniques, such as being glued in place. Indeed, in certain embodiments, the connector 108 may include a separate means (e.g., a latch) for attaching the entire medical device tube 102 to the connector 108. As such, rather than attaching the individual prongs 176 of the connector 108 to the lumens 140 of the medical device tube 102, the prongs 176 may simply slide into the lumens 140, and may be held in place due to the attachment of the connector 108 to the medical device tube 102. In addition, in certain embodiments, the connector 108 may have separate openings that connect to the inner cannula of the medical device tube 102.

As described above, one technique for forming the medical device tube 102 may be extrusion. As such, in extruding the medical device tube 102, the locations on the cross-sectional profile of the medical device tube 102 where the inner wall 134 meets the struts 142 and where the outer wall 136 meets the struts 142 may be somewhat rounded due at least in part to the tendency of the extruded material to adhere to nearby material during the extrusion process. FIG. 14 through FIG. 17 are partial cross-sectional views of the medical device tube 102 illustrating different shapes of the lumens 140. As described above, the lumens 140 are radially equally spaced around the circumference of the medical device tube 102 and extend axially through the medical device tube 102. In addition, all of the lumens 140 have substantially similar sizes and shapes, although the exact geometries may vary slightly due to the positioning of the substantially similar lumens 140 around the circumference of the medical device tube 102. As illustrated, the tubing material between the lumens 140 may not form straight edges with the inner and outer walls 134, 136. Rather, the support structures 180 (e.g., the struts 142) between the lumens 140 may include rounded edges where the support structures 180 connect to the inner and outer walls 134, 136. As described above, the tubing material that forms the inner and outer walls 134, 136 and the support structures 180 includes a flexible synthetic plastic material suitable for use as a tracheal tube.

The inner wall 134 may be defined as the tubing material between an inner surface 182 of the medical device tube 102 and a circumferential line 184 corresponding to the nearest point of the lumens 140 from the inner surface 182 of the medical device tube 102. Similarly, the outer wall 136 may be defined as the tubing material between an outer surface 186 of the medical device tube 102 and a circumferential line 188 corresponding to the nearest point of the lumens 140 from the outer surface 186 of the medical device tube 102. The volume of the support structures 180 (e.g., the volume between the inner and outer surfaces 182, 186 of the medical device tube 102 less the volume of the inner and outer walls 134, 136 of the medical device tube 102 and less the collective volume of the lumens 140 of the medical device tube 102) is less than the collective volume of the lumens 140 of the medical device tube 102. In addition, each of the support structures 180 has a minimum support structure thickness $t_{ss}$ that is less than the largest cross-sectional dimension of each of the lumens 140.

Figure 14:
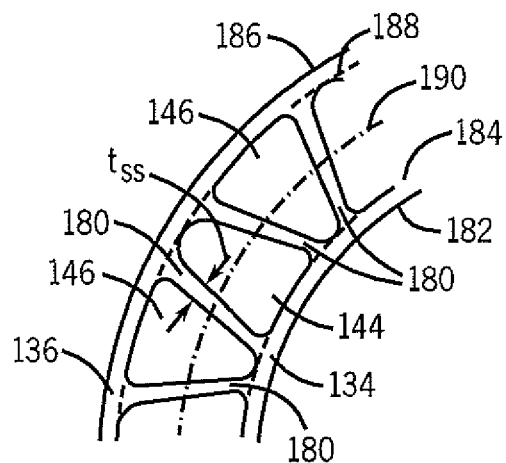
FIG. 14 is a partial cross-sectional view of the medical device tube similar to that illustrated in FIG. 3.

FIG. 14 is a partial cross-sectional view of the medical device tube 102 similar to that illustrated in FIG. 3. As illustrated and described above, the lumens 140 defined by the support structures 180 include a plurality of outer lumens 146 and a plurality of inner lumens 144. In the illustrated embodiment, each of the plurality of outer lumens 146 has a majority of their volume disposed outside of a midline 190, which extends circumferentially midway between the inner surface 182 and the outer surface 186 of the medical device tube 102. Conversely, each of the plurality of inner lumens 144 has a majority of their volume disposed inside of the midline 190. In the illustrated embodiment, each of the lumens 144, 146 has a generally triangular cross section.

Figure 15:
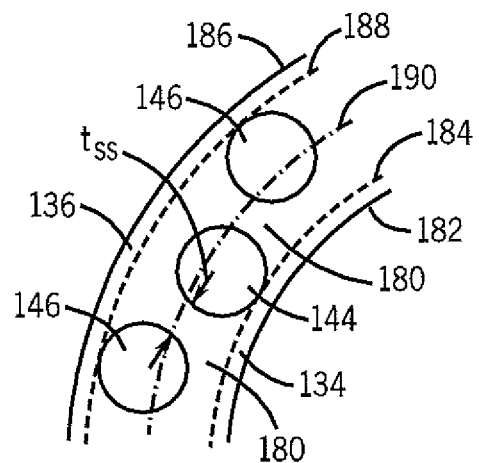
FIG. 15 is a partial cross-sectional view of the medical device tube similar to that of FIG. 14, wherein the lumens have a generally circular cross section.

FIG. 15 is a partial cross-sectional view of the medical device tube 102 similar to that of FIG. 14, wherein the lumens 144, 146 have a generally circular cross section. In particular, the embodiment illustrated in FIG. 15 may be formed using a similar extrusion process as used to create the embodiment illustrated in FIG. 14. However, due to flow characteristics of the tubing material, the types of pins or mandrels used in the extrusion process, the speed of extrusion, and so forth, the shape of the lumens 144, 146 may become generally circular instead of triangular. As with the embodiment illustrated in FIG. 14, each of the plurality of outer lumens 146 has a majority of their volume disposed outside of the midline 190, and each of the plurality of inner lumens 144 has a majority of their volume disposed inside of the midline 190.

Figure 16:
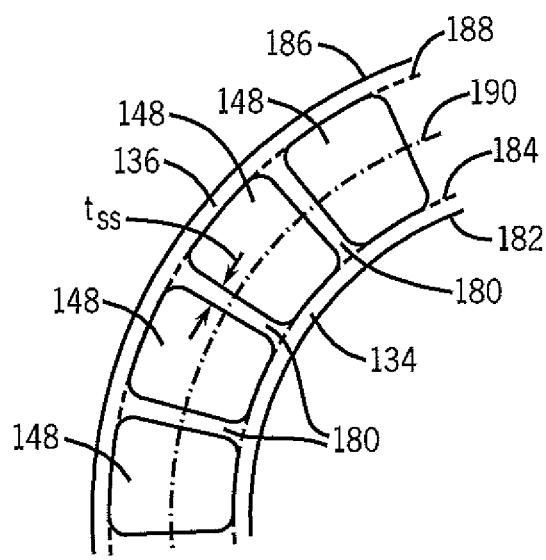
FIG. 16 is a partial cross-sectional view of the medical device tube similar to that illustrated in FIG. 5.
Figure 17:
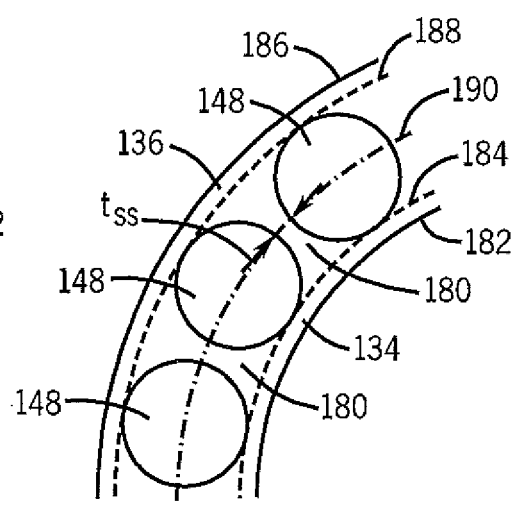
FIG. 17 is a partial cross-sectional view of the medical device tube similar to that of FIG. 16, wherein the lumens have a generally circular cross section.

FIG. 16 is a partial cross-sectional view of the medical device tube 102 similar to that illustrated in FIG. 5. As illustrated and described above, the support structures 180 include a plurality of struts extending generally radially from the inner wall 134 to the outer wall 136 of the medical device tube 102. In the illustrated embodiment, each of the lumens 148 has a generally rectangular cross section. FIG. 17 is a partial cross-sectional view of the medical device tube 102 similar to that of FIG. 16, wherein the lumens 148 have a generally circular cross section. In particular, the embodiment illustrated in FIG. 17 may be formed using a similar extrusion process as used to create the embodiment illustrated in FIG. 16. However, due to flow characteristics of the tubing material, the types of pins or mandrels used in the extrusion process, the speed of extrusion, and so forth, the shape of the lumens 148 may become generally circular instead of triangular.

Figure 18:
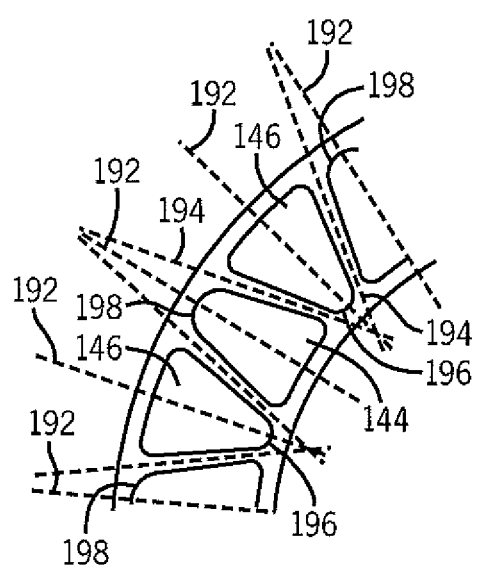
FIG. 18 is a partial cross-sectional view of the medical device tube similar to that illustrated in FIG. 14.
Figure 19:
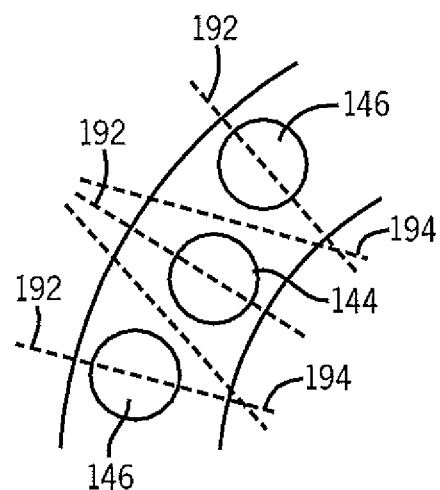
FIG. 19 is a partial cross-sectional view of the medical device tube similar to that illustrated in FIG. 15.

As described above with respect to FIG. 14 and FIG. 15, in certain embodiments, the support structures 180 between the lumens 140 (e.g., the inner lumens 144 and the outer lumens 146) may generally form a zigzag pattern between the inner and outer walls 134, 136. In other words, the support structures 180 may be angled with respect to radial lines extending through the inner lumens 144 and the outer lumens 146. For example, FIG. 18 is a partial cross-sectional view of the medical device tube 102 similar to that illustrated in FIG. 14. Similarly, FIG. 19 is a partial cross-sectional view of the medical device tube 102 similar to that illustrated in FIG. 15. As illustrated in FIG. 18 and FIG. 19, each of the inner and outer lumens 144, 146 may have lines 192 that extend radially through the center of the inner and outer lumens 144, 146. In addition, each of the support structures 180 may include a line 194 that extends through the support structure 180. As illustrated, the lines 194 that extend through the support structures 180 may be angled with respect to the radially lines 192 extending through the inner and outer lumens 144, 146. In addition, as illustrated in FIG. 18, the outer lumens 146 may have an outer lumen apex 196 near the inner wall 134 of the medical device tube 102, whereas the inner lumens 144 may have an inner lumen apex 198 near the outer wall 136 of the medical device tube 102.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A medical device tube, comprising:
   a ventilation lumen having an open distal end for ventilating a patient and extending from the open distal end to a proximal end;
   a continuous and generally circular inner wall encircling the ventilation lumen;
   a continuous and generally circular outer wall; and
   support structures extending continuously along the length of the medical device tube generally from the proximal end to the distal end and between the inner wall and the outer wall, wherein the support structures, the inner wall, and the outer wall form a plurality of radially equally spaced lumens extending axially through the medical device tube, all of the lumens being of substantially the same size and shape, and the support structures having a volume less than the collective volume of the lumens, and wherein the walls and support structures are made of a flexible synthetic plastic material suitable for use as a tracheal tube, and wherein the support structures define a plurality of outer lumens and a plurality of inner lumens, the outer lumens having a majority of their volume disposed outside of a midline extending circumferentially midway between an outer surface of the outer wall and an inner surface of the inner wall, and the inner lumens having a majority of their volume disposed inside of the midline.

2. The medical device tube of claim 1, wherein each lumen has a generally triangular cross section.

3. The medical device tube of claim 1, wherein the support structures comprise a plurality of struts extending generally radially from the inner wall to the outer wall.

4. The medical device tube of claim 1, wherein each of the support structures has a thickness that is less than a largest cross sectional dimension of each of the lumens.

5. The medical device tube of claim 4, wherein the outer wall, the inner wall, and the support structures are made of the same material.

6. The medical device tube of claim 1, comprising at least six self-similar lumens.

7. The medical device tube of claim 6, comprising at least twelve self-similar lumens.

8. A medical device tube, comprising:
   a tubular body having an inner wall, an outer wall, and support structures between the inner wall and the outer wall, wherein the support structures, the inner wall, and the outer wall form a plurality of radially equally spaced lumens extending axially through the medical device tube, all of the lumens being of substantially the same size and shape, and the support structures having a volume less than the collective volume of the lumens, and wherein the walls and support structures are made of a flexible synthetic plastic material suitable for use as a tracheal tube, and wherein the support structures define a plurality of outer lumens and a plurality of inner lumens, the outer lumens having a majority of their volume disposed outside of a midline extending circumferentially midway between an outer surface of the outer wall and an inner surface of the inner wall, and the inner lumens having a majority of their volume disposed inside of the midline; and
   a connector secured to a proximal end of the tubular body.

9. The medical device tube of claim 8, wherein each lumen has a generally triangular cross section.

10. The medical device tube of claim 8, wherein the support structures comprise a plurality of struts extending generally radially from the inner wall to the outer wall.

11. The medical device tube of claim 8, wherein each of the support structures has a thickness that is less than a largest cross sectional dimension of each of the lumens.

12. The medical device tube of claim 11, wherein the outer wall, the inner wall, and the support structures are made of the same material.

13. The medical device tube of claim 8, comprising at least six self-similar lumens.

14. The medical device tube of claim 13, comprising at least twelve self-similar lumens.

* * * * *